(12) United States Patent
Defant et al.

(10) Patent No.: US 10,966,633 B2
(45) Date of Patent: Apr. 6, 2021

(54) WRIST WORN MOBILE ALCOHOL AND OFFENDER MONITORING SYSTEM

(71) Applicant: 3M ELECTRONIC MONITORING LTD., Tel Aviv (IL)

(72) Inventors: John C. Defant, Lago Vista, TX (US); Michael E. Hamerly, Vadnais Heights, MN (US); David S. Segal, Palm Harbor, FL (US); Sharon Cohen, Charlotte, NC (US)

(73) Assignee: 3M ELECTRONICS MONITORING LTD., Tel Aviv (IL)

( * ) Notice: Subject to any disclaimer, the term of this patent is extended or adjusted under 35 U.S.C. 154(b) by 54 days.

(21) Appl. No.: 15/557,319

(22) PCT Filed: Mar. 4, 2016

(86) PCT No.: PCT/US2016/020855
§ 371 (c)(1),
(2) Date: Sep. 11, 2017

(87) PCT Pub. No.: WO2016/144738
PCT Pub. Date: Sep. 15, 2016

(65) Prior Publication Data
US 2018/0049668 A1 Feb. 22, 2018

Related U.S. Application Data

(60) Provisional application No. 62/131,378, filed on Mar. 11, 2015.

(51) Int. Cl.
*A61B 5/1455* (2006.01)
*A61B 5/08* (2006.01)
(Continued)

(52) U.S. Cl.
CPC .............. *A61B 5/082* (2013.01); *A61B 5/097* (2013.01); *A61B 5/1112* (2013.01);
(Continued)

(58) Field of Classification Search
None
See application file for complete search history.

(56) References Cited

U.S. PATENT DOCUMENTS 4,809,810 A * 3/1989 Elfman .............. G01N 33/4972
180/272
2009/0182216 A1 7/2009 Roushey, III et al.
(Continued)

FOREIGN PATENT DOCUMENTS

EP 2 816 352 A1 12/2014

*Primary Examiner* — Eric F Winakur
*Assistant Examiner* — Marjan Fardanesh
(74) *Attorney, Agent, or Firm* — Soroker Agmon Nordman (57) ABSTRACT

The present disclosure includes a body-worn alcohol detection device. The device includes a housing comprising an electronics module and an alcohol detection module. The device further comprises a strap for securing the housing to a limb of the user. The electronics module includes a processor and a communication module, and the alcohol detection module includes an alcohol detection sensor, a sample collection device and a biometric camera for capturing an image of the inside of the user's mouth.

26 Claims, 4 Drawing Sheets

(51) Int. Cl.
  *A61B 5/00*       (2006.01)
  *A61B 5/097*      (2006.01)
  *A61B 5/11*       (2006.01)
  *G01N 33/497*     (2006.01)
  *A61B 5/1171*     (2016.01)
  *A61B 5/01*       (2006.01)

(52) U.S. Cl.
  CPC .......... *A61B 5/1171* (2016.02); *A61B 5/4845* (2013.01); *A61B 5/681* (2013.01); *A61B 5/6831* (2013.01); *G01N 33/4972* (2013.01); *A61B 5/0002* (2013.01); *A61B 5/0022* (2013.01); *A61B 5/0059* (2013.01); *A61B 5/01* (2013.01)

(56) References Cited

U.S. PATENT DOCUMENTS

| | | |
|---|---|---|
| 2010/0251804 A1 | 10/2010 | Morley et al. |
| 2013/0021153 A1 | 1/2013 | Keays |
| 2013/0035602 A1 | 2/2013 | Gemer |
| 2014/0081106 A1 | 3/2014 | Shnaper et al. |
| 2014/0165697 A1 | 6/2014 | Mochizuki et al. |
| 2014/0311215 A1* | 10/2014 | Keays .................. B60K 28/063 73/23.3 |
| 2014/0365142 A1 | 12/2014 | Baldwin |
| 2015/0084774 A1* | 3/2015 | Wojcik .................. A61B 5/082 340/573.1 |

\* cited by examiner

WRIST WORN MOBILE ALCOHOL AND OFFENDER MONITORING SYSTEM

CROSS REFERENCE TO RELATED APPLICATIONS

This application is a national stage filing under 35 U.S.C. 371 of PCT/US2016/020855, filed 4 Mar. 2016, which claims the benefit of Provisional Application No. 62/131,378, filed 11 Mar. 2015, the disclosure of which is incorporated by reference in its/their entirety herein.

TECHNICAL FIELD

The present disclosure relates to the field of alcohol monitoring. More specifically, the present disclosure relates to the field of mobile breath alcohol monitoring.

BACKGROUND

Alcohol monitoring plays an important role in a variety of fields, ranging from monitoring the use of alcohol for individuals working in occupations, such as healthcare or transportation, where alcohol and drug testing is a regular event associated with monitoring released offenders with alcohol use restrictions and participants in rehabilitation programs.

Alcohol presence can be tested through a variety of methods, including testing urine samples, blood samples, transdermal testing and breath testing. Breath testing often includes analyzing saliva included in exhaled breath for indicators of alcohol. Both blood and urine testing can be invasive and present challenges to perform quickly or in a public setting. Transdermal monitoring can be expensive and may result in inadvertent alcohol detection or false positives.

Breath alcohol testing is commonly used in a multitude of applications because of its convenience and low cost. Typically, breath alcohol testers require a person to blow a sample of breath into a testing device. Within an electrochemical cell, ethanol present in the breath sample is oxidized to acetic acid by the atmospheric reduction of oxygen and converted into an electrical current by a microprocessor contained in a testing device. A person's alcohol usage is determined based upon a comparison between the electrical current calculated from the alcohol content in their breath to predetermined values that are stored in the testing device.

Breath alcohol testing presents several challenges. For example, with many current breath alcohol testers, there is no way to confirm the location or identity of the individual completing the test with the testing device alone. Further, even with breath alcohol testing devices that may include cameras peripherally connected to the testing device for capturing an image of the person's face, the image is often recorded and visual inspection is used to confirm the individual's identity after the test has concluded. At times, when the identity of a person is verified by an image of their face, the person can substitute a photograph or use another mechanism to tamper with the identification method. An improved breath alcohol testing system would be welcomed.

SUMMARY

The present disclosure provides both a handheld and a wrist-worn alcohol detection device. The alcohol detection device provides new methods for confirming the identity of the person providing a sample to the alcohol detection device. The present disclosure provides several advantages including, but not limited to, the identification and confirmation of a user's identity without the need for manual or visual inspection in a compact, an integrated device, and concurrently determining the presence of alcohol contained in the breath of the user. Peripherally connected system components, such as cameras or other biometric sensors (i.e., fingerprint), would not be required to authentic or confirm the identity of the user. This minimization of system components reduces the form factor of the testing device, decreases inaccuracies that may be captured or reported, and lessens the probability that the testing device is tampered.

Specifically, the present disclosure includes a body-worn alcohol detection device. The device includes a housing comprising an electronics module and an alcohol detection module. The device further comprises a strap for securing the housing to a limb of the user. The electronics module includes a processor and a communication module, and the alcohol detection module includes an alcohol detection sensor, a sample collection device and a biometric camera for capturing an image of the inside of the user's mouth.

In another aspect, the present disclosure includes an alcohol detection device. The device comprises a housing comprising an electronics module and an alcohol detection module. The electronics module includes a processor and a communication module. The alcohol detection module includes an alcohol detection sensor and sample collection device and a biometric camera for capturing an image of the inside of a user's mouth.

In another aspect, the present disclosure includes a body-worn alcohol detection device. The device includes a housing comprising an electronics module and an alcohol detection module and a strap for securing the housing to a limb of a wearer. The electronics module includes a communication module. The alcohol detection module includes an alcohol detection sensor and a sample collection device. The sample collection device includes at least one light source and at least one light detector.

In another aspect, the present disclosure includes an alcohol detection device. The device includes a housing comprising an electronics module and an alcohol detection module. The electronics module includes a communication module. The alcohol detection module includes an alcohol detection sensor and sample collection device. The sample collection device includes at least one light source and at least one light detector. Optionally, the alcohol detection device includes a remote processing device that alerts a user through at least one of the following communication means: SMS message, telephone, or email, to provide a sample to the device.

BRIEF DESCRIPTION OF DRAWINGS

The following figures provide illustrations of the present invention. They are intended to further describe and clarify the invention, but not to limit scope of the invention.

DETAILED DESCRIPTION

Figure 1:
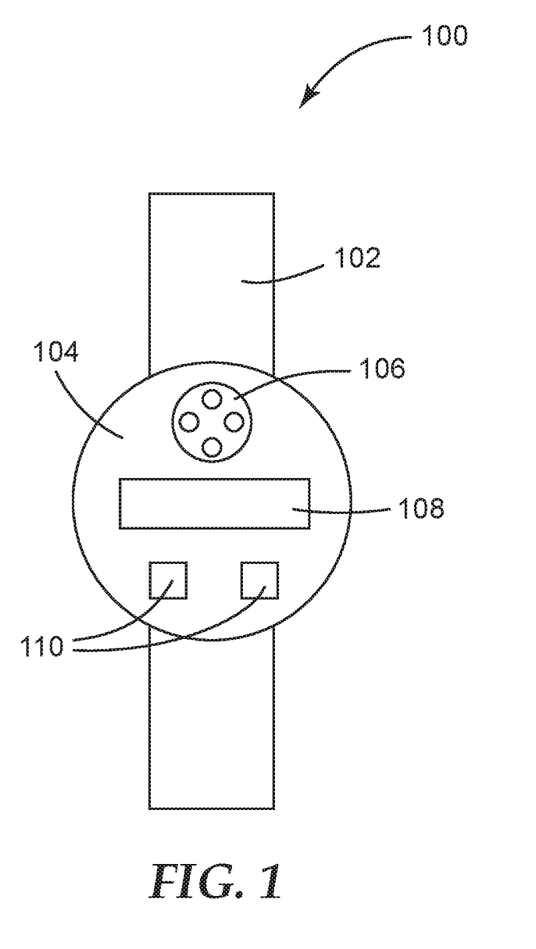
FIG. 1 is an exemplary mobile alcohol detection device.

FIG. 1 is an exemplary mobile alcohol detection device 100. Mobile alcohol detection devices can take several forms, including handheld and body-worn devices. Device 100 is a body-worn device. More specifically, device 100 is designed to be worn on the wrist of a user. Device 100 includes strap 102, housing 104, alcohol detection module 106, which includes an alcohol detection sensor, a sample collection device and a biometric camera for capturing an image of the inside of the user's mouth. Device 100 further includes a user interface, including both a display 108 and buttons 110. Display 108 may include one or more different types of devices for presenting information (e.g., instructions to operate device 100) to a user. Display 108 may include any number of visual (e.g., liquid crystal display or light emitting diode) or audible (e.g., one or more speakers) feedback devices. Buttons 110 provide a mechanism to interact with device 100 and/or respond to instructions presented on the display 108. Buttons 110 may be physically present on device 100 or contained within display 108 through soft or touch interaction. Placement of the alcohol detection module 106, display 108, and buttons 110 is exemplary and other location configurations or arrangements on the mobile alcohol detection 100 are within the scope of the present disclosure.

While device 100 is shown as a wrist worn device, device 100 can also be a handheld device, or can be configured in any other way consistent with the present disclosure. Handheld device may not include the same components as a wrist worn device 100. For example, a handheld device 100 may not include strap 102.

Figure 2:
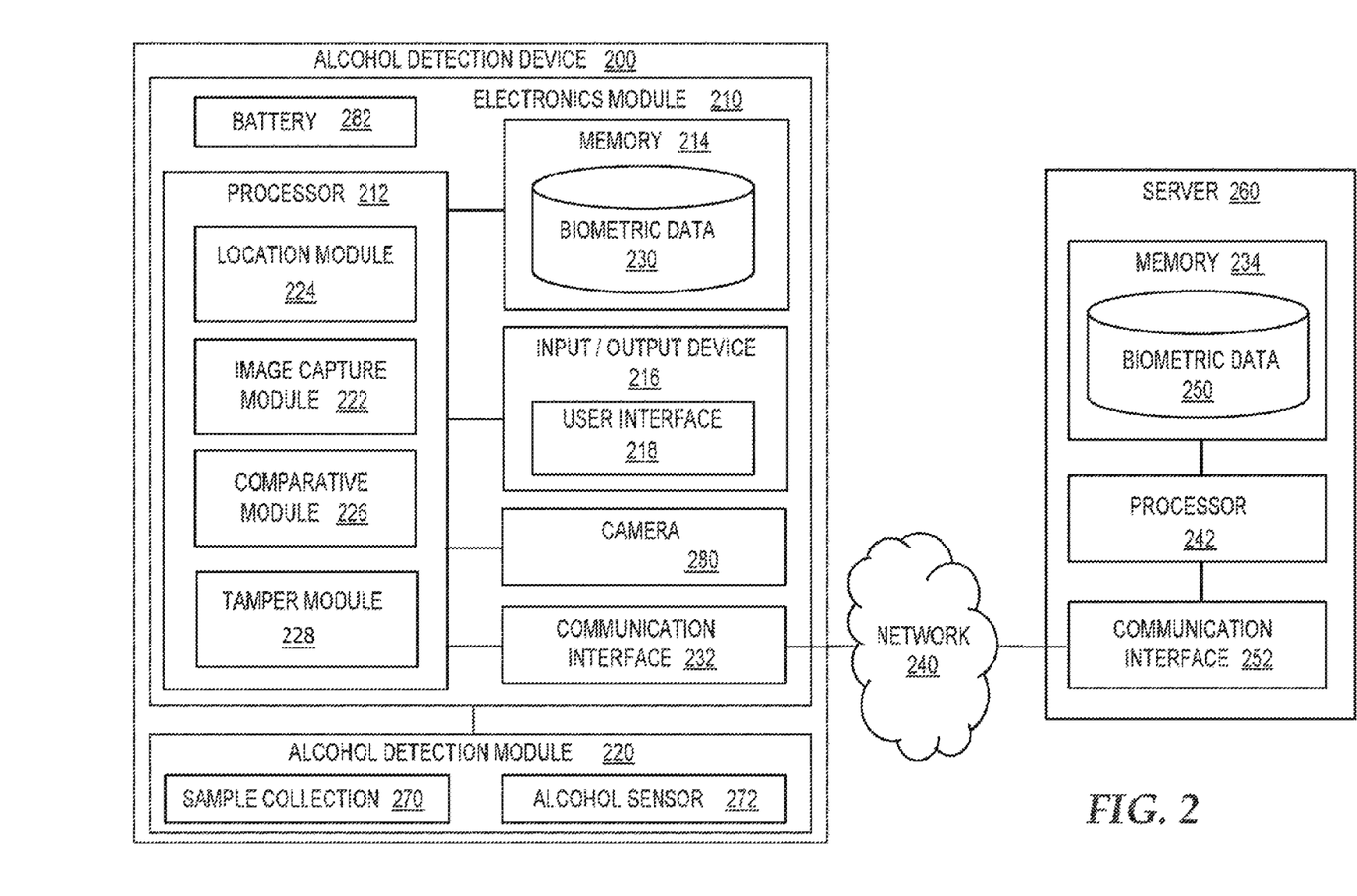
FIG. 2 block diagram of mobile alcohol detection device and a server.

FIG. 2 shows a block diagram of an alcohol detection device 200. Device 200 includes electronics module 210. Electronics module 210 includes processor 212, power source 282, memory 214, input/output device 216, camera 280 and communication interface 232. Device 210 further includes alcohol detection module 220. Alcohol detection module 220 includes a sample collection device 270 and an alcohol sensor 272.

While the illustrated alcohol detection device 210 includes a variety of modules and components within the electronics module 210 and alcohol detection module 220, a device within the scope of the present invention may include a subset of the described modules and components. A device within the scope of the present invention may have additional modules and components. A device within the scope of the present invention may have a varying arrangement of modules and components. For example, the alcohol detection module 220 may be part of electronics module 210.

Processor 212 may include, for example, one or more general-purpose microprocessors, specially designed processors, application specific integrated circuits (ASIC), field programmable gate arrays (FPGA), a collection of discrete logic, and/or any type of processing device capable of executing the techniques described herein. In some embodiments, processor 212 (or any other processors described herein) may be described as a computing device. In some embodiments, memory 214 may be configured to store program instructions (e.g., software instructions) that are executed by processor 212 to carry out the techniques described herein. In other embodiments, the techniques described herein may be executed by specifically programmed circuitry of processor 212. Processor 212 can perform a variety of functions and contain a variety of modules. For example, processor 212 may include an image capture module 222, a location module 224, a comparative module 226 and a tamper module 228.

Image capture module 222 interfaces with camera 280 to capture and process images of the inside of the user's mouth. Image capture module 222, as managed by the processor 212, may transmit and receive commands to 1) trigger camera 280 to capture an image and 2) perform image processing techniques on a captured image from camera 280 such as calibration, normalization, cropping, classification, feature or pattern extraction, color correction, gray scaling, or projection. Various image processing techniques may be used to place the captured image into a common or standardized format for ease of comparison to other captured images, which will be described in further detail with respect to the operation of the comparative module 226. For example, image capture module 222 may receive a captured image from camera 280 that is 540×540 pixels and through cropping image processing techniques may reduce the captured image to 320×320 pixels. Other image processing may be performed on the image once captured and methods to enhance or modify would be apparent to one of skill in the art.

Location module 224 captures location information related to the location of the device 200. Such location information may include proximity location or absolute location information or both. For example, proximity location information may include information indicating that the device 200 is within a certain proximity of another device. An example of such information occurs when device 200 is tethered through radio frequency (RF) or some other mode of communication to a stationary unit, such as a base station permanently installed in a location such as a person's residence. When device 200 is in communication with the base unit, the location module provides proximity location information indicating that the device 200 is within a pre-defined radius of the base station such as described in commonly owned and assigned U.S. Pat. No. 6,998,985, which is hereby incorporated by reference in its entirety. Absolute location information can indicate where device 200 as defined geographically. This information can be generated using location technologies such as components receive satellite signals and determine location using, for example, GPS or the Global Navigation Satellite System (GLONASS) such as described in commonly owned and assigned U.S. Pat. No. 6,853,304, which is hereby incorporated by reference in its entirety. A location module may use other location technologies such as triangulation using local WiFi signals or other known location technologies to estimate location of the device 200, and thereby the location of the person wearing or using the device.

Comparative module 226 can be used to compare an image of the inside of a user's mouth captured by camera 280 to a stored image for that user to confirm the user's identity. In some embodiments, device 200 may also include a second camera configured to capture an image of a user's face while the user is providing a sample to the sample collection device. One or both of the captured image from inside of the user's mouth or the captured image of the user's face can be compared with a reference image by comparative module 226 to confirm the identity of the user. In one example, the reference image may be stored on the device 200 as biometric data 230 in memory 214. In an alternate embodiment, a captured image, whether of the inside of a user's mouth or of a user's face can be transmitted to a remote processing device, such as a server 260, and the server can confirm the identity of the user by comparing the captured images to reference images stored as biometric data 250 in memory 234.

Tamper module 228 can detect tamper with the device 200. For example, tamper module 228 may be used to transmit a signal, such as an infrared signal, through a strap on the device and receive the signal on the other end of the strap such as described in commonly owned and assigned U.S. Pat. No. 6,853,304. If the signal is not received, the tamper module 228 may send an alert the user interface 218 and/or to a remote server 260 to indicate that device 200 has been tampered with. Tamper module 228 may also detect whether a user is using the correct tube, straw or other mechanism to provide a sample to sample collection device 270 by detecting light that is reflected from device 200, through a straw, tube, or other sample collection device and back to receptors on device 200. The use of a reflective sample collection device 270 ensures that the user's mouth is accurately aligned with camera 280, so that camera 280 can capture the desired features within a user's mouth. Further, reflective sample collection device 270 ensures that there is a continuous physical connection between the mouth of the user providing a saliva sample and the camera 280 so that a substitute saliva sample cannot be provided to the device 200 in an attempt to fool the device 200.

Power source 282 can be used to provide power to any component of device 200 that requires power. Power source 282 may be a disposable battery such that device 200 is designed to be disposed of once power source 282 is depleted. In another embodiment, power source 282 may be a rechargeable battery, such as a lithium-ion or nickel-cadmium battery that may hold its charge for a period of time and may be recharged by a user upon depletion, on a regular schedule or as necessary. Power source 282 may also be primarily or ancillary provided by energy harvesting means such as solar, thermal, or electromagnetic. As an example, device 200 may include circuitry in the form of antennae and capacitors to capture electromagnetic radiation, convert to measurable signals (e.g., current or voltage), and store the signal in a capacitor or super-capacitor device to provide power for the components and modules.

Memory 214 is used to store information related to the device 200, the user, and other information necessary for device 200 to adequately monitor the user. For example, memory 214 may store biometric data 230 related to a user to whom the device 200 is registered. Biometric data 230 may include one or more images of a user's face, oral, and dental characteristics. Facial images may include landmarks or features for identifying a user's face. Position, size, and/or shape of the eyes, nose, cheekbones, lips, and jaw may be used to biometrically identify a user by facial features. Other anatomical features of the face may also by captured and analyzed in the present disclosure such as the shape or location of veins. One or more images of the mouth may include position, size, and/or shape of the tongue, soft or hard palate, oropharynx, tonsils, or uvula. Other anatomical features of the mouth may also be captured and analyzed in the present disclosure. One or more dental images to identify a user may include position, size, and/or shape of the gingival tissue or teeth. Memory 214 may also optionally store temperature data as a scalar or a range of values (e.g., minimum to maximum) associated with the breath or anatomical feature of the user. Such biometric data 230 can be reference images. In another embodiment, biometric data can be specific reference points that are compared to reference points gleaned from an image captured by device 200 to confirm the identity of a user of device 200. Memory 214 may include any volatile or non-volatile storage elements. Examples may include random access memory (RAM) such as synchronous dynamic random access memory (SDRAM), read-only memory (ROM), non-volatile random access memory (NVRAM), electrically erasable programmable read-only memory (EEPROM), and FLASH memory.

Camera 280 may be a small camera integrated into the face of device 200 such that camera 280 is aligned to capture an image the inside of a user's mouth during or before or after a user providing a saliva sample to sample collection device 270. In some embodiments, camera 280 is aligned to capture an image at the end of a tube or straw through which a user is required to provide a sample. Tube or straw can be configured to be securely connected to device such that the misalignment or misuse of the tube or straw is indicative of tamper of the device 200. Camera 280 may be Charge Coupled Device (CCD) or Complementary Metal-Oxide Semiconductor (CMOS) varieties, color sensing devices or the like. An example of an image sensor for camera 280 is S55K9A1-HD ⅛" 1.4 .mu.m BSI pixel image sensor available from Samsung of Samsung Town, Seoul, South Korea.

Alcohol detection module 220 can include a variety of components, including sample collection device 270 and alcohol sensor 272. Sample collection device 270 is a device or component that serves as an interface through which a user provides a breath or saliva sample, and/or is a receptacle into which a user provides a breath or saliva sample. Sample collection device 270 is mated to alcohol sensor 272 so that alcohol sensor 272 can determine whether the sample provided to or through sample collection device 270 includes indications of alcohol, which may be used to estimate blood alcohol content (BAC). When a user provides a breath sample through the tube to the sample collection device 270 any ethanol present in the breath is oxidized to acetic acid at the anode of the alcohol sensor 272. At the cathode of the alcohol sensor 272 atmospheric oxygen is reduced, with an overall reaction of oxidation of ethanol into acetic acid and water. The reaction produces an electrical current which is measured by the alcohol sensor 272 and sent to the processor 212. Processor 212 compares the measured electrical current to data stored in memory 214 to determine and/or estimate the BAC of the device 200 user. Alcohol sensors 272 that use other techniques to detect the presence of alcohol (i.e., without oxidation) may also be used. The alcohol detection module 220 may also include a sensor to record the temperature of the breath sample. Processor 212 compares the recorded temperature to data stored in memory 214 to determine variation upper or below an expected value. An example of a temperature sensor for alcohol detection module 270 is LM35DZ LM35 Centigrade Temperature Sensor IC from National Semiconductor of Lewisville, Tex.

Server 260 is an example of a remote server that can be in communication with alcohol detection device 200. Server 260 includes memory 234, processor 242 and communication interface 252. Server 260 may operate within a local network or be hosted in a Cloud computing environment. Communication interface 252 can communicate with device 200 through a variety of types of networks 240, including WiFi, cellular, Bluetooth, Bluetooth low energy, or the like. Memory 234 can include a variety of information, such as device history information, enrollment information for a user of device 200, biometric data 250 for a user of device 200, historic location or other device status information, device repair history, and rules or other monitoring restrictions associated with a user of device 200. Biometric data 250 may contain the same data as was described for biometric data 230 of the device 200. Processor 242 can be used to process information related to device 200. For example, in one embodiment, processor 242 may do comparative analysis, comparing a captured image to a reference image or comparing data mined from a captured image to reference data for a particular user. Processor 242 may include, for example, one or more general-purpose microprocessors, specially designed processors, application specific integrated circuits (ASIC), field programmable gate arrays (FPGA), a collection of discrete logic, and/or any type of processing device capable of executing the techniques described herein. In some embodiments, processor 242 (or any other processors described herein) may be described as a computing device. In some embodiments, memory 234 may be configured to store program instructions (e.g., software instructions) that are executed by processor 242 to carry out the techniques described herein. In other embodiments, the techniques described herein may be executed by specifically programmed circuitry of processor 242. Memory 234 may include any volatile or non-volatile storage elements. Examples may include random access memory (RAM) such as synchronous dynamic random access memory (SDRAM), read-only memory (ROM), non-volatile random access memory (NVRAM), electrically erasable programmable read-only memory (EEPROM), and FLASH memory In some configurations, when device 200 detects tamper, indication of alcohol, or any other status or action requiring an alert, device 200 may signal both a local alert by providing such an alert to user interface 218 to be displayed to a user. Device 200 may also, or instead, transmit an alert to server 260 to provide external notification of an incident. External notification may include notification of a monitoring database or monitoring center, emergency health professionals, law enforcement, parole officers or any other designated recipient of an alert or notification.

Input/output device 216 may include one or more devices configured to input or output information from or to a user or other device. In some embodiments, the input/output device 216 may present a user interface 218 where a user may configure the operation of or receive instructions from the device 200. For example, the user interface 218 may include a display screen for presenting visual information to a user. In some embodiments, the display screen includes a touch sensitive display. In some embodiments, a user interface 218 may include one or more different types of devices for presenting information to a user. The user interface 218 may include, for example, any number of visual (e.g., display devices, lights, etc.), audible (e.g., one or more speakers), and/or tactile (i.e., buttons) feedback devices. In some embodiments, the input/output devices 216 may represent one or more of a display screen (e.g., a liquid crystal display or light emitting diode display) and/or a printer (e.g., a printing device or component for outputting instructions to a printing device). In some embodiments, the input/output device 216 may be configured to accept or receive program instructions (e.g., software instructions) that are executed by the processor 212 to carry out the embodiments described herein.

Communication interface 232 can communicate with server 260 through a variety of types of networks 240, including WiFi, cellular, Bluetooth, Bluetooth low energy, or the like.

Figure 3:
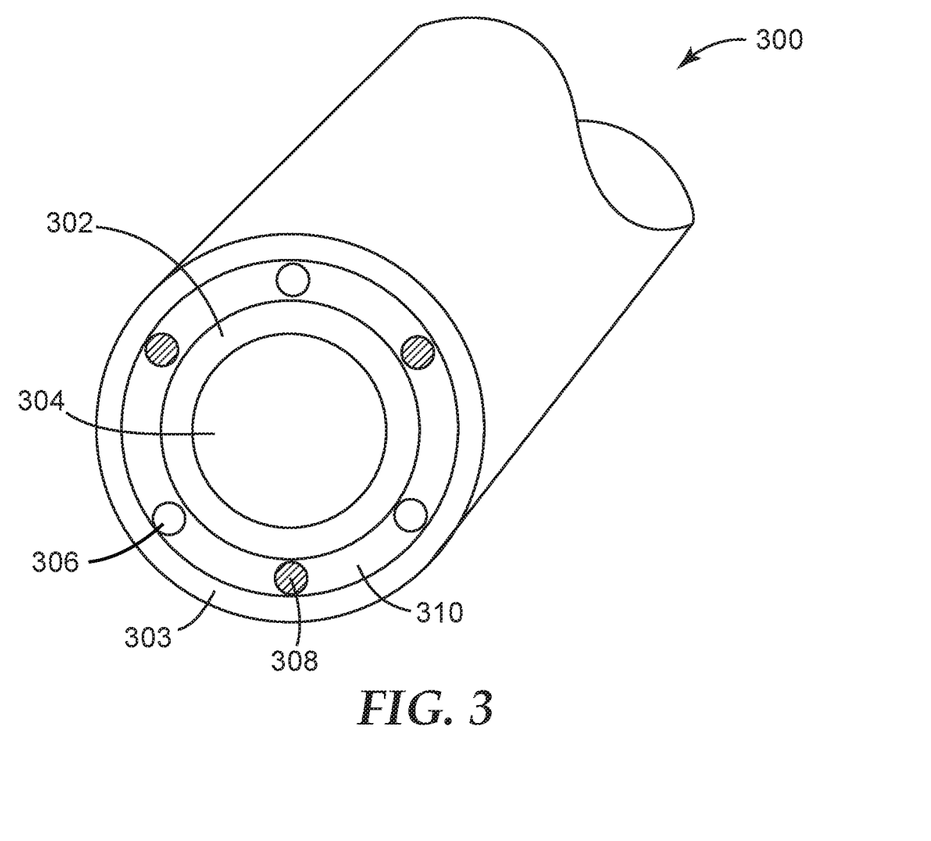
FIG. 3 is an exemplary reflective tube.

FIG. 3 is an exemplary reflective tube 300. In some embodiments, reflective tube may be used to ensure a continuous connection between the mouth of a user providing a sample and the device described herein. Further, it ensures the tube is of the proper dimensions to allow a camera in the device to capture an image of the user's mouth. Tube 300 includes several layers including hollow channel 304, interior layer 302, film layer 310 and exterior layer 303. Embedded in film layer 310 are optic inputs 306 and optic outputs 308 that are aligned with light sources from the tamper module of an alcohol detection device as described herein. The tube is constructed in multiple layers. The outer layer is a protective covering made from opaque material, such as high density polyethylene or polyvinyl chloride, to hide the internal construction. Inside the outer layer are multiple fiber optic light guide pipes running parallel to the length of the tube assembly, and arranged in a circular array around the diameter of the tube. These pipes are arranged in such a way that it is not easy to drill a hole from the outer opaque cover to the inside of the tube without passing through at least one fiber optic light guide. The ends of each fiber light guide are coated with a metallic film so that light that is injected in the other end of the fiber will reflect back to the source. The non-coated end of the fiber is brought to the end of the tube assembly where it is inserted in the alcohol detection module 220. In this way, light emitting diodes (LEDs) can inject light into each fiber and the amount of light reflected back may be measured determining if someone has tampered with the tube by drilling a hole into the tube and disrupting the light reflectance of one of the fibers. Inside the ring of fiber optic light guides is another fiber optic strand used to image the inside of the user's mouth. The pipe extends the length of the tube and is fitted with a lens at each end to allow a camera in the alcohol detection module 220 to receive an image from the other end of the tube inserted in the user's mouth. Finally, the tube assembly contains a hollow tube extending the length of the tube assembly to allow the user's breath to be sampled by the alcohol detection module 220.

Figure 4:
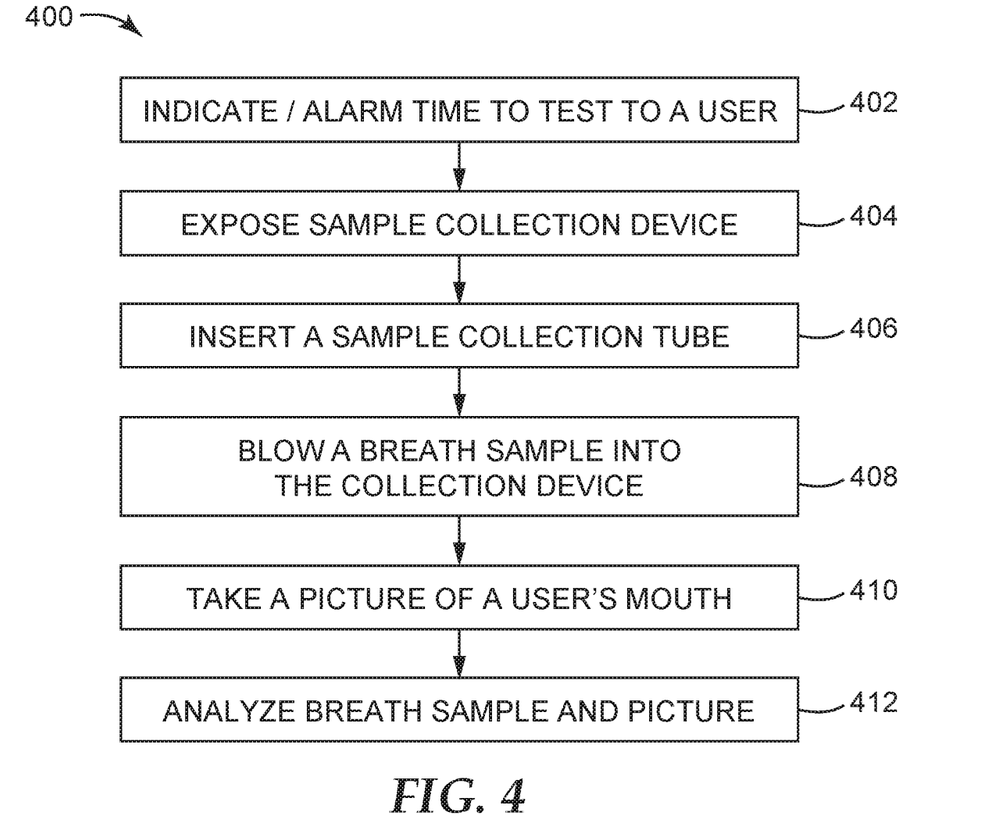
FIG. 4 is an exemplary flow chart for using a mobile alcohol detection device.

FIG. 4 is an exemplary flow chart 400 for using a mobile alcohol detection device. In step 402, the device indicates to the user that a test is required. The device may provide an indication through an auditory or visual alarm or alert. The device may provide a set amount of time in which the user must complete the test. In some instances, the device may instruct or require a user to acknowledge the alarm or alert through means such as pressing a button or providing another response through the user interface.

In step 404, the device exposes the sample collection device to the user. This may occur by the device exposing an opening through which it will absorb the user's breath sample. The device exposes the sample collection device 270 to the user. This may occur by the device loading a new collection tube into the sampling sensor and then exposing it to the user through an opening in the device. Alternately, the device may present the user with the collection tube through an opening and the user will be required to insert the tube in the sample collection sensor, similar to inserting a straw into opening in the device. The device may also include a locking mechanism or electromechanical latch to prevent insertion of the sample collection device 270 until the user is notified to conduct the test. The device may absorb the breath sample directly, or through a tube, such as the one illustrated in FIG. 3.

In step 406, the user inserts a sample collection tube into the device. The tube may be inserted so that it is properly aligned with the camera and any other tamper features included in the device.

In step 408, the user blows into the sample collection device, thus providing a breath sample to the alcohol detection module.

At or near the same time as step 408, in step 410, the camera captures an image of the inside of the user's mouth.

In step 412, the alcohol detection module analyzes the breath sample and the device analyzes the image of the user's mouth that was captured by the camera. If the image, or certain features of the image, does not match the stored for the designated user, the device may trigger a local alert or a remote alert indicating tamper.

If the alcohol detection module detects indications of alcohol in the breath sample, the device may also trigger a local alert or a remote alert. The alert may be indicative of violation of parole or other alcohol-related restrictions the user is subject to. If an alcohol alert is triggered, the user may be required to go to a location where they must complete a verifying alcohol test.

Figure 5:
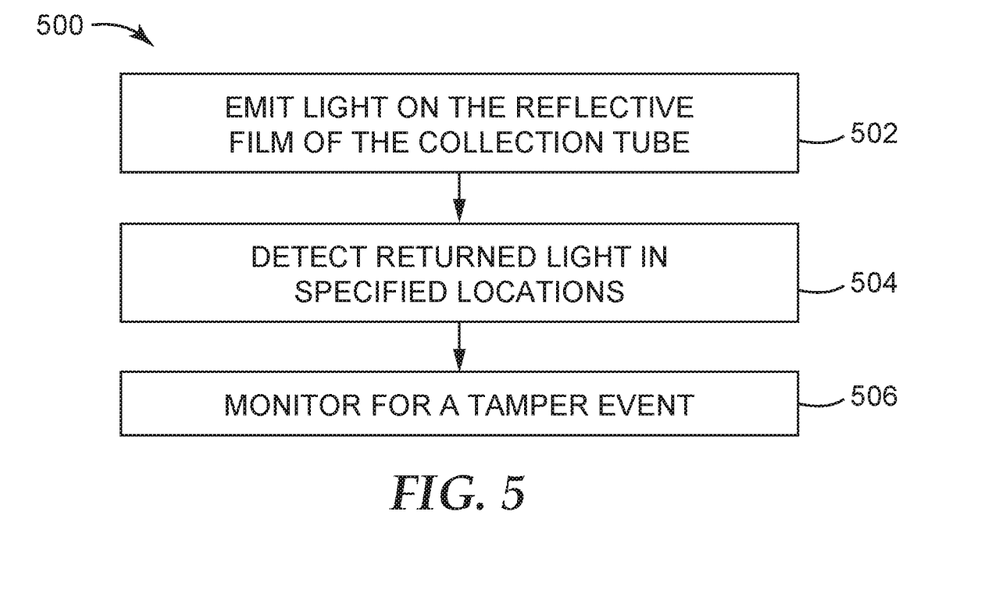
FIG. 5 is an exemplary flow chart for detecting tamper with a reflective tube.

FIG. 5 is an exemplary flow chart 500 for detecting tamper with a reflective tube. In step 502, the device emits light on the film layer of the collection tube. The light emitted may be from an LED or similar light emitting device, such as a laser, and may be in the visible, infrared (IR), or ultraviolet (UV) spectrum. The light may be directed through a lens (e.g., concave or convex) or other focusing/magnifying mechanism into the tube's fiber optic light guides. In step 504, the device detects returned light reflected back from the end of each fiber optic light guide. In step 506, the device monitors for a tamper event. A tamper event may include drilling through the side wall of the tube assembly disrupting the ability of a particular fiber optic light guide to reflect light off the metallized end.

The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Variations on the present disclosure will be apparent to one of skill in the art upon reading the present disclosure, and are intended to be included within the scope of the present disclosure. For example, a variety of electronic components may be used as within the device. A variety of films and constructions for the tube may also be used consistent with the present invention.

What is claimed is:

1. A body-worn alcohol detection device comprising:
a housing comprising an electronics module and an alcohol detection module;
a strap for securing the housing to a limb of a user;
wherein the electronics module includes a processor, a communication module and a biometric camera for capturing an image of the inside of the user's mouth;
wherein the alcohol detection module includes an alcohol detection sensor and a sample collection device; and
wherein the alcohol detection device further comprises a reflective tube to ensure a continuous connection between the user's mouth and the alcohol detection device;
wherein the reflective tube includes several layers including an exterior layer, a film layer and an interior layer enclosing a hollow channel;
wherein the film layer comprises multiple fiber optic light guide pipes running parallel to a length of the reflective tube and arranged in a circular array around the hollow channel.

2. The device of claim 1, wherein the strap comprises a tamper detection feature.

3. The device of claim 1, wherein the electronics module further includes a location module.

4. The device of claim 1, wherein the electronics module further includes a rechargeable battery.

5. The device of claim 1, wherein the alcohol detection device is configured to transmit the captured image to a remote processing device for comparing with a reference image to confirm the identity of the user.

6. The device of claim 1, wherein the alcohol detection device is configured to compare the captured image with the reference image by a comparative model of the alcohol detection device.

7. The device of claim 1, wherein the alcohol collection device further comprises a user interface to alert the user to provide a sample to the sample collection device.

8. The device of claim 1, including a remote processing device that alerts a user through at least one of the following communication means: SMS message, telephone, or email, to provide a sample to the sample collection device.

9. The device of claim 1, wherein the communication module is configured to report results from the alcohol detection sensor to a remote processing device or a designated monitoring officer.

10. The device of claim 1, wherein the device further comprises an exterior camera and wherein the exterior camera is positioned to take a picture of at least a portion of the user's face.

11. The device of claim 1, wherein the alcohol detection module is configured to measure the temperature of the sample to confirm it coincides with the temperature of exhaled breath.

12. The device of claim 1, wherein the exterior layer 303 comprises a protective covering made from an opaque material to hide internal construction of the reflective tube.

13. The device of claim 1, wherein the multiple fiber optic light guide pipes are arranged so that at least one fiber optic light guide pipe will be damaged if drilling a hole from the exterior layer to the hollow channel.

14. The device of claim 1, wherein ends of some fiber light guide pipes are coated with a metallic film so that light that is injected from a light source in another end of the fiber light guide pipes will reflect back to the light source to detect tampering.

15. The device of claim 1, wherein some fiber optic light guide pipes are fitted with a lens at each end to receive an image of the user's mouth with the biometric camera.

16. A mobile alcohol detection device comprising:
a housing comprising an electronics module and an alcohol detection module;
wherein the electronics module includes a communication module and a biometric camera for capturing an image of the inside of a user's mouth;
wherein the alcohol detection module includes an alcohol detection sensor and a sample collection device; and
wherein the alcohol detection device further comprises a reflective tube to ensure a continuous connection between the user's mouth and the alcohol detection device;
wherein the reflective tube includes several layers including an exterior layer, a film layer and an interior layer enclosing a hollow channel;
wherein the film layer comprises multiple fiber optic light guide pipes running parallel to a length of the reflective tube and arranged in a circular array around the hollow channel.

17. The device of claim 16, wherein the electronics module further includes a location module.

18. The device of claim 16, wherein the electronics module further includes a rechargeable battery.

19. The device of claim 16, wherein the alcohol detection device is configured to transmit the captured image to a remote processing device for comparing with a reference image to confirm the identity of the user.

20. The device of claim 16, wherein the alcohol detection device is configured to compare the captured image with the reference image by a comparative model of the alcohol detection device.

21. The device of claim 16, wherein the alcohol detection device further comprises a user interface to alert the user to provide a sample to the sample collection device.

22. The device of claim 16, including a remote processing device that alerts a user through at least one of the following communication means: SMS message, telephone, or email, to provide a sample to the sample collection device.

23. The device of claim 16, wherein the communication module is configured to report results from the alcohol detection sensor to a remote processing device or a designated monitoring officer.

24. The device of claim 16, wherein the device further comprises an exterior camera and wherein the exterior camera is positioned to take a picture of at least a portion of the user's face.

25. The device of claim 16, wherein the alcohol detection module is configured to measure the temperature of the sample to confirm it coincides with the temperature of exhaled breath.

26. The device of claim 16, wherein the device is handheld.

* * * * *